United States Patent
Eberler et al.

(10) Patent No.: US 9,316,708 B2
(45) Date of Patent: Apr. 19, 2016

(54) PATIENT SUPPORT APPARATUS FOR A MEDICAL IMAGING APPARATUS AND A MEDICAL IMAGING APPARATUS HAVING THE PATIENT SUPPORT APPARATUS

(75) Inventors: Ludwig Eberler, Neumarkt Ld.OPf. (DE); Razvan Lazar, Erlangen (DE); Volker Matschl, Bamberg (DE); Jürgen Nistler, Erlangen (DE); Wolfgang Renz, Erlangen (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 365 days.

(21) Appl. No.: 13/540,688

(22) Filed: Jul. 3, 2012

(65) Prior Publication Data
US 2013/0008726 A1   Jan. 10, 2013

(30) Foreign Application Priority Data
Jul. 4, 2011   (DE) .................. 10 2011 078 567

(51) Int. Cl.
- G01G 19/52 (2006.01)
- G01R 33/28 (2006.01)
- G01G 19/44 (2006.01)
- A61B 5/055 (2006.01)
- G01R 33/54 (2006.01)

(52) U.S. Cl.
CPC ........... *G01R 33/288* (2013.01); *A61B 5/0555* (2013.01); *G01G 19/445* (2013.01); *G01R 33/543* (2013.01)

(58) Field of Classification Search
CPC .. G01G 19/445; A61B 5/0555; G01R 33/288; G01R 33/543
USPC ................................ 177/144; 5/601
See application file for complete search history.

(56) References Cited

U.S. PATENT DOCUMENTS

| | | | | |
|---|---|---|---|---|
| 4,802,541 | A * | 2/1989 | Bator et al. | 177/212 |
| 5,789,713 | A * | 8/1998 | Wakasa et al. | 177/25.13 |
| 5,861,582 | A * | 1/1999 | Flanagan et al. | 177/144 |
| 6,026,318 | A * | 2/2000 | Bernstein et al. | 600/427 |
| 6,441,324 | B1 * | 8/2002 | Stimpson | 177/137 |
| 6,987,227 | B2 * | 1/2006 | Wakasa | 177/25.13 |
| 7,437,787 | B2 * | 10/2008 | Bhai | 5/613 |
| 7,505,803 | B2 * | 3/2009 | Boese et al. | 600/407 |
| 7,569,780 | B2 * | 8/2009 | Von Arb et al. | 177/210 R |
| 7,682,079 | B2 * | 3/2010 | Schwartz et al. | 378/209 |
| 7,906,737 | B2 * | 3/2011 | Freydank et al. | 177/25.13 |
| 2006/0173273 | A1 | 8/2006 | Boese et al. | |
| 2009/0143703 | A1 * | 6/2009 | Dixon et al. | 600/587 |
| 2009/0252300 | A1 | 10/2009 | Coe | |
| 2010/0176800 | A1 * | 7/2010 | Biber et al. | 324/207.13 |
| 2012/0038484 | A1 * | 2/2012 | Dixon et al. | 340/666 |
| 2014/0000032 | A1 * | 1/2014 | Dixon et al. | 5/611 |

FOREIGN PATENT DOCUMENTS

DE    102005004142 A1    8/2006

* cited by examiner

*Primary Examiner* — Peter Macchiarolo
*Assistant Examiner* — Natalie Huls

(57) ABSTRACT

A patient support apparatus for a medical imaging apparatus, such as a magnetic resonance apparatus, is proposed. The patient support apparatus has a couch, a lifting unit for vertical movement of the couch, a travel unit, and at least one sensor unit to detect at least one weight variable for determining the weight of a patient. The at least one sensor unit has at least one sensor element, which is disposed on the lifting unit and/or on the travel unit.

15 Claims, 3 Drawing Sheets

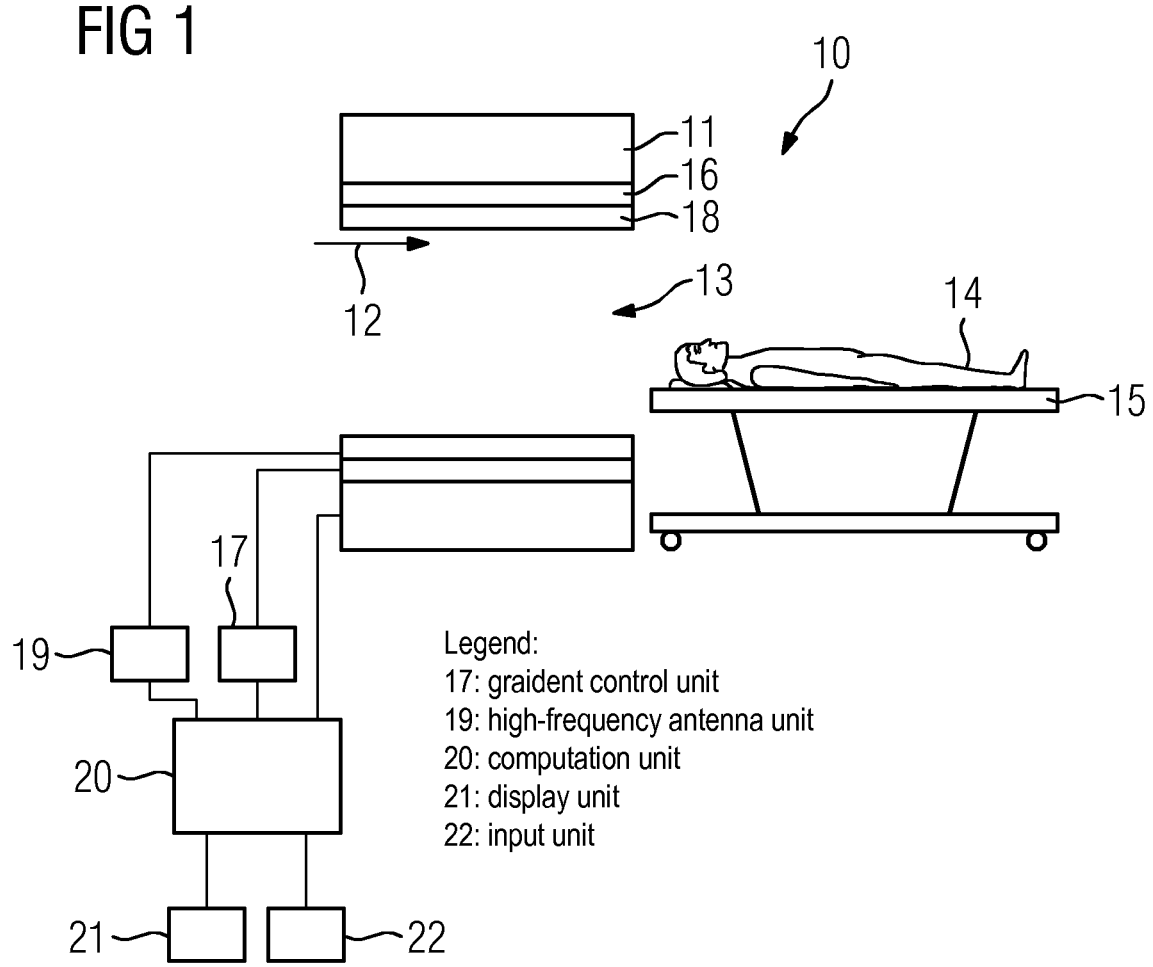

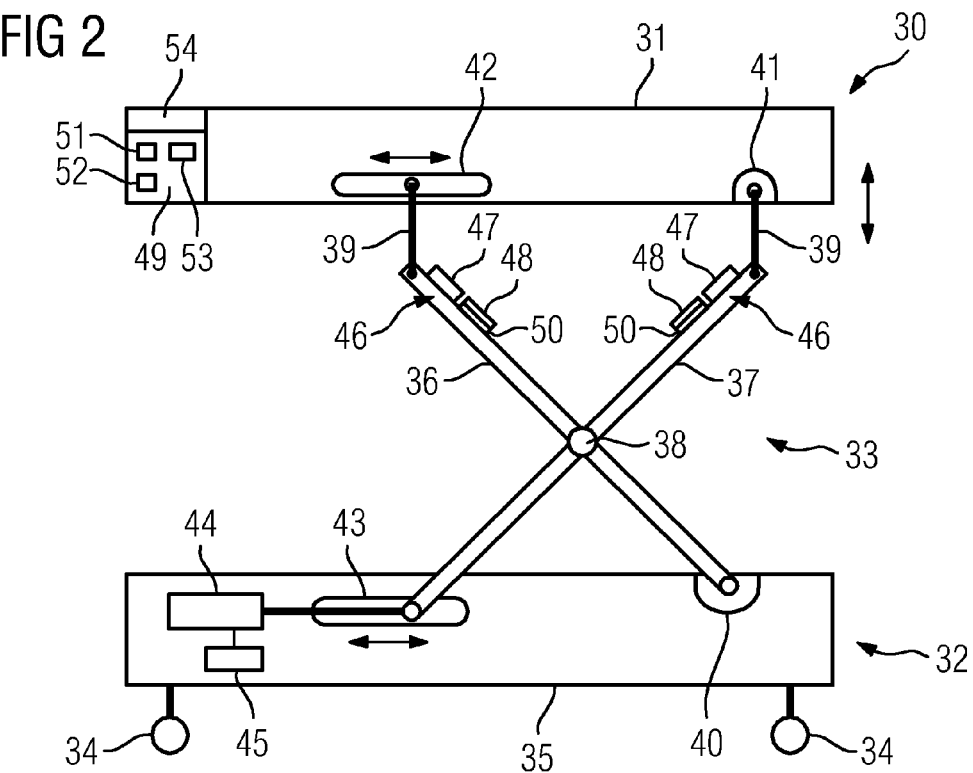
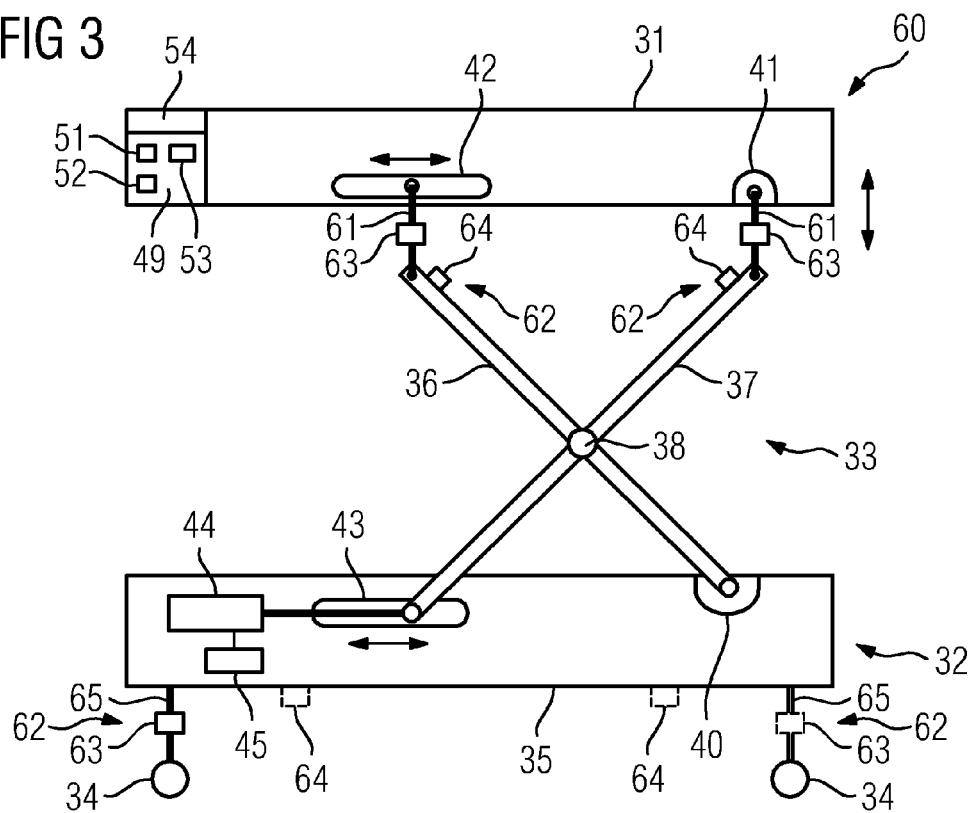

PATIENT SUPPORT APPARATUS FOR A MEDICAL IMAGING APPARATUS AND A MEDICAL IMAGING APPARATUS HAVING THE PATIENT SUPPORT APPARATUS

CROSS REFERENCE TO RELATED APPLICATIONS

This application claims priority of German application No. 10 2011 078 567.1 filed Jul. 4, 2011, which is incorporated by reference herein in its entirety.

FIELD OF INVENTION

The present application relates to a patient support apparatus for a medical imaging apparatus, having a couch, a lifting unit for vertical movement of the couch, a travel unit, and having at least one sensor unit to detect at least one weight variable for determining the weight of a patient.

BACKGROUND OF INVENTION

For medical imaging, such as for magnetic resonance imaging, it is necessary to take account of the weight of a patient when calculating a specific absorption rate SAR. An approximately correct value for the patient's weight not only increases patient comfort during the medical imaging examination but also enhances patient safety during the medical imaging examination. If calculations are based on an incorrect value for patient weight, this can cause the body of the patient to become undesirably hot for example during the medical imaging examination.

To detect the weight of the patient, until now it has been known for the patient to be asked his/her weight before the medical imaging examination and for this to be input manually when registering the patient for the medical imaging examination. However if the patient cannot be consulted or if the inputting of patient weight is overlooked before the medical imaging examination, an estimated value is input for patient weight for example.

SUMMARY OF INVENTION

The object of the present application is to provide a patient support apparatus, with which the weight of a patient can be determined quickly and accurately. The object is achieved by the features of the independent claims. Varies embodiments are disclosed in the dependent claims.

The application is based on a patient support apparatus for a medical imaging apparatus, such as a magnetic resonance apparatus, having a couch, a lifting unit for vertical movement of the couch, a travel unit, and having at least one sensor unit to detect at least one weight variable for determining the weight of a patient.

It is proposed that the at least one sensor unit has at least one sensor element, which is disposed on the lifting unit and/or on the travel unit. In this context a vertical movement of the couch refers to a movement of the couch, which is aligned along or counter to the force of the weight of the couch. A lifting unit also refers to a unit which can execute a translatory movement of components, such as a vertical movement of the couch, by at least one lifting element, which can be formed for example by a lifting column and/or scissor lifting mechanism. The translatory movement can be generated mechanically and/or pneumatically and/or hydraulically, etc., within the lifting element. The lifting unit comprises a drive unit. The travel unit has a chassis, with the at least one sensor element for example being disposed in a region of a wheel suspension unit of the travel unit. The weight variable here can be a variable, which can be used to determine the weight of the patient, it being possible for the weight variable to be formed by an electrical variable, a mechanical variable and/or further variables deemed expedient by the person skilled in the art. The embodiment allows the weight of the patient to be determined quickly and reliable and also prevents incorrect estimates of patient weight. The weight of the patient can also be determined automatically after the patient has been laid and/or positioned on the couch, so that the correct patient weight is always available for a medical imaging examination. It is possible to adjust and/or set a specific absorption rate individually for the patient for the upcoming magnetic resonance measurement based on the available accurate patient weight.

It is also proposed that the lifting unit has at least one force transmission element, the at least one sensor element of the at least one sensor unit being disposed at least partially on the force transmission element. It is possible here to determine the at least one weight variable based on a force transmission, such as based on a movement and/or change of movement and/or change of position of the force transmission element. It is for the force transmission element to be disposed between the lifting unit and the couch for a force transmission.

It is further proposed that the at least one sensor element of the at least one sensor unit is formed at least partially by the at least one force transmission element of the lifting unit. The at least one sensor element can be integrated within the lifting unit, saving additional space, assembly outlay and costs. Alternatively the at least one sensor element can also be formed at least partially by a force transmission element of the travel unit.

It is for the at least one sensor element to be disposed on a drive unit for movement of the lifting unit. The drive unit comprises an electric motor or further units to convert electrical energy to mechanical energy.

If the at least one sensor element is formed at least partially by a strain gauge, the at least one weight variable can be detected simply and economically. In this context a strain gauge refers to a sensor element for detecting shape changes due to stretching, with an electrical resistance of the strain gauge changing due to shape changing and/or stretching.

In a further embodiment of the application the at least one sensor element can also be formed at least partially by a piezo element, so that the at least one weight variable can be detected simply and economically. A piezo element here refers to an element and/or component, the mode of operation of which is based on the piezo-electric effect, whereby a change of electric polarization and thus the occurrence of an electrical voltage takes place in solid bodies when the solid body changes shape elastically or the solid body changes shape when an electrical voltage is applied to it.

It is further proposed that the at least one sensor element is formed at least partially by an energy detection element, with the result that energy generated in a drive unit for movement of the couch and/or to maintain a position of the couch can be detected. The at least one weight variable is formed here by an energy variable, it being possible to determine the weight of the patient based on the energy variable alone or together with a distance traveled due to the movement of the couch.

In one embodiment of the application it is proposed that the at least one sensor unit has at least one further sensor element, configured with the same structure as the first sensor element for a reference measurement. It is thus possible to eliminate interference signals from the measurement signals. It is possible thus to detect interference signals, which are produced by a magnetic field of a medical imaging apparatus configured as a magnetic resonance apparatus, for example hysteresis effects and/or Hall effects, etc., produced within the sensor element, and eliminate them from the measurement signals in this manner.

It is further proposed that the at least one sensor element and the at least one further sensor element are disposed directly adjacent to one another, thereby allowing the most accurate and effective detection possible of the interference signals within the at least one sensor element, in that the at least one further sensor element is subject to essentially the same interference signals and/or interference effects as the at least one sensor element to detect the weight variable. The further sensor element is disposed on the lifting unit and/or on the travel unit in such a manner that during positioning of the patient on the couch and/or a mechanical movement of the lifting unit and/or an energy output from the drive unit the at least one further sensor element of the sensor unit is spared a shape change and/or a change in any physical characteristic, for example a voltage value.

The at least one sensor unit has a signal filter unit, which filters interference signals out of the sensor signals, with the result that the at least one weight variable can be detected as accurately as possible and therefore the weight of the patient can be determined accurately from the at least one weight variable. The interference signals are produced for example by a magnetic field of the magnetic resonance apparatus and/or a magnetic gradient field within the at least one sensor element.

It is further proposed that the at least one sensor unit has a computation unit, thereby allowing quick evaluation of the weight variables for a determination of patient weight. The computation unit has a processor and/or a memory unit for example.

In a further embodiment of the application it is proposed that the at least one sensor unit has at least one local coil detection unit. A local coil detection unit in this context refers to a unit which can be used to detect the number and/or type of local coils disposed around the patient on the patient support apparatus for the magnetic resonance measurement. The embodiment allows the weight of the local coils, which are used for the current magnetic resonance measurement, to be subtracted simply from a total weight determined by the sensor unit, thereby allowing the weight of the patient to be determined as accurately as possible.

It is also possible to detect a weight distribution of the patient on the couch, thereby contributing to the safety of the patient on the couch and/or the safe transportation of the patient on the couch, if the patient support apparatus has an overload unit, which determines a weight distribution on the couch as a function of at least weight variables. To this end the at least one sensor unit has at least two sensor elements and at least three sensor elements, so that the weight variables can be detected at different positions on the couch.

The application is based on a medical imaging apparatus, such as a magnetic resonance apparatus, having a patient support apparatus. During magnetic resonance examinations it is necessary to indicate patient weight accurately for precise setting of the specific absorption rate, so that incorrect settings can be prevented in respect of patient weight.

The application is also based on a method for determining patient weight by a sensor unit, which is disposed within a lifting unit of a patient support apparatus, having the following method steps:
  detecting at least one first weight variable,
  lying and/or positioning the patient on a couch of the patient support apparatus and
  detecting at least one second weight variable by the sensor unit, the at least one second weight variable being different from the at least one first weight variable due to the force of the weight of the patient acting on the couch surface.

The method allows the weight of the patient to be determined quickly and reliably. The weight of the patient can also be determined in a time-saving manner, as by lying and/or positioning the patient on the couch of the patient support apparatus it is possible to detect the weight variables automatically and determine the patient weight.

Accurate detection of the weight of the patient can be achieved, if at least one reference variable is detected and the reference variable is used to eliminate interference signals from the at least one first and/or second weight variable. The reference variable is detected without the action of a force and/or load, so that only interference signals and/or noise signals can be detected by the at least one reference variable.

The at least one reference variable can be detected here at the same time as detection of the at least one first and/or the at least one second weight variable, so that current interference influences on the at least one first and/or the at least one second weight variable can always be detected. Alternatively it is also possible for the at least one reference variable to take place before a medical imaging examination and/or before detection of the at least one first and/or the at least one second weight variable. For example detection of the at least one reference variable can take place once a day when the medical imaging apparatus is started up or the at least one reference variable can take place before the medical imaging examination, such as the magnetic resonance examination, for the respective patient.

It is further proposed that a weight distribution on the couch of the patient support apparatus is determined in an evaluation step, thereby allowing a hazard situation for the patient and/or the medical imaging apparatus to be identified. For example the risk of the patient support apparatus overturning can be identified by the weight distribution.

An accurate weight distribution can be achieved, if weight variables are detected at two different positions at least on the patient support apparatus for the determination of the weight distribution. However it is for weight variables to be detected at three different positions at least on the patient support apparatus.

It is also proposed that a warning signal is generated and output if the weight distribution is irregular, thereby enhancing the safety of the patient support apparatus, in that an operator for example, such as a clinician, can be warned about a hazard situation in respect of the patient support apparatus and/or the patient.

BRIEF DESCRIPTION OF THE DRAWINGS

Further features and details of the application will emerge from the exemplary embodiments described in the following and the drawings, in which:
FIG. 1 shows a schematic representation of a medical imaging apparatus having a patient support apparatus,
FIG. 2 shows a first exemplary embodiment of the patient support apparatus,
FIG. 3 shows a second exemplary embodiment of the patient support apparatus.

DETAILED DESCRIPTION OF INVENTION

Figure 4:
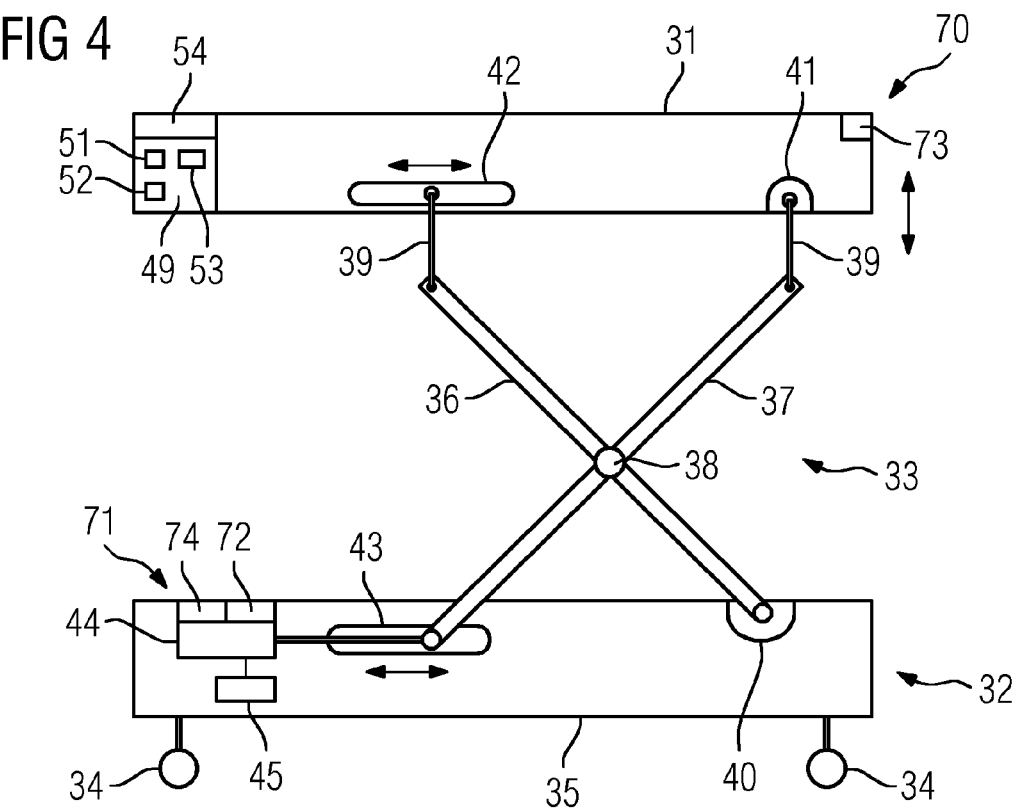
FIG. 4 shows a third exemplary embodiment of the patient support apparatus and
  FIG. 5 shows a method for determining patient weight.

FIG. 1 shows a medical imaging apparatus formed by a magnetic resonance apparatus 10. Alternatively the medical imaging apparatus can also be formed by a computed tomography apparatus, a PET apparatus and/or further medical imaging apparatuses deemed expedient by the person skilled in the art.

The magnetic resonance apparatus 10 comprises a main magnet 11 for generating a powerful and constant main magnetic field 12. The magnetic resonance apparatus 10 also has a cylindrical accommodating region 13 to accommodate a patient 14, the accommodating region being enclosed by the main magnet 11 in a circumferential direction. The patient 14 can be moved into the accommodating region 13 by a patient support apparatus 30 of the magnetic resonance apparatus 10. To this end the patient support apparatus 30 is disposed in a movable manner within the magnetic resonance apparatus 10.

The magnetic resonance apparatus 10 also has a gradient coil 16 for generating magnetic field gradients, which is used for spatial encoding during imaging. The gradient coil 16 is controlled by a gradient control unit 17. The magnetic resonance apparatus 10 also has a high-frequency antenna 18 and a high-frequency antenna unit 19 for exciting polarization, which becomes established in the main magnetic field 12 generated by the main magnet 11. The high-frequency antenna 18 is controlled by the high-frequency antenna unit 19 and emits high-frequency magnetic resonance sequences into an examination space, which is essentially formed by the accommodating region 13. This deflects the magnetization from its equilibrium position. Magnetic resonance signals are also received by the high-frequency antenna unit 19.

To control the main magnet 11, the gradient control unit 17 and to control the high-frequency antenna unit 19, the magnetic resonance apparatus 10 has a control unit formed by a computation unit 20. The computation unit 20 controls the magnetic resonance apparatus 10 centrally, for example performing a predefined imaging gradient echo sequence. Control information, such as imaging parameters for example, and reconstructed magnetic resonance images can be displayed on a display unit 21, for example on at least one monitor, of the magnetic resonance apparatus 10 for an operator of the magnetic resonance apparatus 10. The magnetic resonance apparatus 10 also has an input unit 22, which can be used by an operator to input information and/or parameters during a measurement process.

The illustrated magnetic resonance apparatus 10 can of course comprise further components, as are normally present in magnetic resonance apparatuses 10. A general mode of operation of a magnetic resonance apparatus 10 is also known to the person skilled in the art, so there is no need for a detailed description of the general components here.

FIG. 2 shows a first exemplary embodiment of the patient support apparatus 30. The patient support apparatus 30 has a couch 31, on which the patient 14 is positioned for an examination. The patient support apparatus 30 also has a travel unit 32 and a lifting unit 33. In the present exemplary embodiments the travel unit 32 has four travel elements 34, formed in each instance by wheels. The patient support apparatus 30 can be moved by the four wheels. The travel unit 32 also has a base unit 35. The base unit 35 is configured as cuboidal with a rectangular base area. Alternatively the base unit 35 can also be formed by a rectangular frame. The four wheels are disposed on a side of the base unit 35 facing away from the lifting unit 33.

In the present exemplary embodiments (FIGS. 1 to 4) the lifting unit 33 is formed by a scissor lifting unit. Alternatively the lifting unit 33 can also be formed by a lifting column unit and/or further lifting units 33 deemed expedient by the person skilled in the art. The lifting unit 33 is provided for vertical movement of the couch 31, the couch 31 being moved along or counter to the force of a weight acting on the couch 31 by the lifting unit 33. The lifting unit 33 here is disposed between the travel unit 32 and the couch 31.

The lifting unit 33 has a first lifting element 36 and a second lifting element 37, which are formed by force transmission elements for transmitting a force from the lifting unit 33 to the couch 31. The two lifting elements 36, 37 are connected along a longitudinal extension of the first and second lifting elements 36, 37 so that they can be moved rotationally in a center, for example by a rotational joint 38 of the lifting unit 33. A rotation axis is configured here perpendicular to the longitudinal extension of the two lifting elements 36, 37 and also perpendicular to the plane of the drawing in FIGS. 2 to 4. The first lifting element 36 and the second lifting element 36 here are configured in the manner of rods. At one end facing the base unit 35 in each instance the two lifting elements 36, 37 are supported in the base unit 35. At one end of the two lifting elements 36, 37 facing the couch 31 in each instance a force transmission element 39 of the lifting unit is disposed on both lifting elements 36, 37 respectively, the first lifting element 36 and the second lifting element 37 being supported by the force transmission elements 39 in the couch 31. The force transmission elements 39 are connected rotationally to the respective lifting element 36, 37 by a rotational joint of the lifting unit. A rotation axis of the rotational joints is aligned parallel to the rotation axis of the rotational joint 38 between the two lifting elements 36, 37.

The base unit 35 and the couch 31 each have a fixed bearing unit 40, 41 and a sliding bearing unit 42, 43 to support the two lifting elements 36, 37. The first lifting element 36 is supported by its end facing the base unit 35 in the fixed bearing 40 of the base unit 35, the first lifting element 36 here being supported in such a manner that it can be rotated about a rotation axis, which is aligned parallel to the rotation axis of the rotational joint between the two lifting elements 36, 37. The second lifting element 37 is also supported by the force transmission element 39 disposed at the end facing the couch 31 in the fixed bearing 41 of the couch 31.

The end of the second lifting element 37 facing the base unit 35 is supported in the sliding bearing 43 of the base unit 35. The sliding bearing unit 43 has a longish hollow space, in which the second lifting element 37 is supported in such a manner that it can be moved along a longitudinal extension of the hollow space. The sliding bearing 42 disposed within the couch 31 also has a longish hollow space. The first lifting element 36 is supported within the hollow space by the force transmission element 39 in such a manner that it can be moved along a longitudinal extension of the hollow space.

For stability of the couch 31 it is conceivable for the patient support apparatus 30 to have at least two or more lifting units 33 as illustrated above, disposed parallel to one another between the base unit 35 and the couch 31.

An area of the base unit 35 facing the couch 31 and an area of the couch 31 facing the base unit 35 are disposed parallel to one another by the lifting unit 33. For vertical movement of the couch 31 along the force of gravity, the lifting unit 33 has a drive unit 44, which is formed by an electric motor. The drive unit 44 is disposed within the base unit 35 and converts electrical energy to mechanical energy, which is transmitted by an energy transmission element to the second lifting element 37. The lifting unit 33 also has a control unit 45, which controls the drive unit 44 and movement of the lifting unit 33. The control unit 45 is similarly disposed within the base unit 35. The drive unit 44 is used to generate a drive for movement of the second lifting element 37 within the sliding bearing 43 of the base unit 35, which initiates a parallel movement of the first lifting element 36 in the sliding bearing 42 of the couch 31 and thus a vertical movement of the couch 31. Vertical movement of the couch 31 changes the distance between the couch 31 and the base unit 35.

The couch 31 is used to determine the weight of a patient 14. To this end the couch 31 has a sensor unit 46. The sensor unit 46 has a number of sensor elements 47, 48, just four of the sensor elements 47, 48 being illustrated in FIG. 2. The first two sensor elements 47 are designed to detect weight variables and in the present exemplary embodiment are formed by strain gauges. The strain gauges are disposed on the lifting unit 33, with one strain gauge being disposed in each instance on an end of the lifting elements 36, 37 facing the couch 31. The strain gauges supply weight variables in each instance in the form of an electrical variable, the value of which is a function of a force acting on the sensor unit 46, for example a stretching force due to the arrangement of the strain gauges on the lifting elements 36, 37. An electrical resistance value of the strain gauges is detected to detect the weight variable. The strain gauges are attached to the lifting elements 36, 37 by adhesion.

When the patient 14 is laid and/or positioned on the couch 31, the force of the weight of the patient 14 acts on the lifting unit 33 in addition to the force of the weight of the couch 31. The force of the weight of the patient 14 additionally acting on the lifting unit 33 causes a shape change at the lifting elements 36, 37, which is detected by the first sensor elements 47. A mechanical shape change is also produced at the strain gauges, causing a change in an electrical resistance within the strain gauge and thus a change in the weight variable.

The sensor unit 46 also has a computation unit 49, which calculates the weight of the patient 14 from the sensed weight variables of the sensor elements 47. The computation unit 49 here is integrated within the couch 31 and connected by a data transmission unit (not shown in detail) to the individual sensor elements 47, 48 of the sensor unit 46.

The two further sensor elements 48 of the sensor unit 46 are likewise formed by strain gauges and are thus configured with the same structure as the first two sensor elements 47. These further sensor elements 48 are configured as reference sensor elements and are designed for a reference measurement, so that unwanted interference signals, generated for example due to the main magnetic field applied in the magnetic resonance apparatus 10 and/or the gradient field applied in the magnetic resonance apparatus 10 within the sensor elements 47, 48, are detected. These interference signals can be produced for example due to a hysteresis effect and/or a Hall effect within the sensor elements 47, 48. Due to acoustic injection the applied gradient field can also produce a higher noise component within the detected sensor signal. To detect the reference signal, one of the two reference sensor elements in each instance is disposed directly adjacent to one of the two sensor elements 47 on the lifting elements 36, 38, so that the reference sensor elements are subject to essentially the same interference signals and interference influences as the first two sensor elements 47. To decouple the two reference sensor elements from any shape change on the part of the lifting elements 36, 37, a decoupling element 50 is disposed in each instance between the lifting elements 36, 37 and the reference sensor elements, for example an elastomer.

To eliminate the interference signals from the detected sensor signals, the sensor unit 46 also has a signal filter unit 51. This signal filter unit 51 is encompassed by the computation unit 49 and can be formed for example by a bridge circuit and/or an electronic differentiator.

Local coils around the patient 14 can also be disposed on the couch 31 with the patient 14. These local coils would falsify a weight measurement. To prevent this, the sensor unit 46 has a local coil detection unit 52. The local coil detection unit 52 can for example receive information about the local coils being used by a data exchange with the computation unit 20 of the magnetic resonance apparatus 10 and/or based on plug-type contacts, which must connect the local coils to the patient support apparatus 30 for a magnetic resonance measurement.

The patient support apparatus 30 also has an overload unit 53, which determines a weight distribution on the couch 31 based on the weight variables of the sensor elements 47. The overload unit 53 is integrated within the computation unit 49. The different positions of the individual sensor elements 47 mean that a weight variable can be detected at different positions on the couch 31. The overload unit 53 determines the weight distribution from the different weight variables of the sensor elements 47.

To determine the weight of the patient 14, detection 100 of a first weight variable takes place first, before the patient 14 is positioned on the couch 31. The first weight variable can be detected by the sensor elements 47 and then be stored in a memory unit of the computation unit 49 or can be a known variable, which is read out of the memory unit. The weight of the empty couch 31 is determined from the first weight variable. The patient 14 is then positioned 101 on the couch 31 of the patient support apparatus 30. The local coils required for the upcoming magnetic resonance examination are also positioned on the patient 14. After the patient 14 has been positioned on the couch 31, detection 102 of a second weight variable takes place by each of the sensor elements 47. The second weight variables are different from the first weight variables due to the force of the weight of the patient 14 and of the local coils acting on the sensor elements.

At the same time as the detection 100, 102 of the first and/or second weight variables by the sensor elements 47, the reference sensor elements are also read out to detect a reference weight variable. Alternatively the reference weight variable can also take place before the detection of the first and/or second weight variable by the sensor elements 47, so there is then no need to use reference sensor elements. Detection of the reference weight variable can take place once a day when the magnetic resonance apparatus 10 has been started up.

In a subsequent evaluation step 103 the computation unit 49 first eliminates the interference signals from the first and/or second weight variables and calculates the weight of the patient 14 based on the first and second weight variables. Also in the evaluation step 103 when calculating the weight of the patient 14 a mass and/or weight of the local coils used for the upcoming magnetic resonance examination is/are subtracted from the total weight calculated.

In the evaluation step 103 a weight distribution on the couch 31 is also calculated by the overload unit 53. In this process the weight variables detected at different positions are taken into account in the calculation of the weight distribution on the couch 31. In the evaluation step 103 the weight distribution of the couch 31 is also evaluated in respect of a possible hazard situation for the patient positioned on the couch 31 and/or for the couch 31, for example overturning of the patient support apparatus 30 and/or too heavy a load on the couch 31, with which the safety of the patient 14 can no longer be ensured, and/or the couch 31 is moved up against an obstacle, causing the couch 31 to become jammed. If the evaluation of the weight distribution of the couch 31 indicates a hazard situation, a warning signal is generated and output by the overload unit 53. The warning signal can be formed by an acoustic and/or an optical warning signal, which is output for example by a display unit 54 of the patient support apparatus 30 to the operator. The overload unit 53 is also designed to execute a safety shutdown in the event of an acute hazard situation. The safety shutdown for example causes vertical movement of the couch 31 to be stopped and/or the wheels of the travel unit 32 to be locked.

FIGS. 3 and 4 show alternative exemplary embodiments of the patient support apparatus. Essentially identical components, features and functions are in principle shown with identical reference characters. The description which follows is essentially limited to the differences in relation to the exemplary embodiment in FIG. 2, with reference being made to the description of the exemplary embodiment in FIG. 2 for identical components, features and functions.

FIG. 3 shows an alternative embodiment of a patient support apparatus 60 to the one in FIG. 2. The patient support apparatus 60 has a couch 31 and a travel unit 32, which are configured in the same way as the couch 31 and travel unit 32 in FIG. 2. The patient support apparatus 60 also has a lifting unit 33 with two lifting elements 36, 37, which are configured and supported in the same way as in the description relating to FIG. 2. Force transmission elements 61 are disposed respectively between the first and second lifting elements 36, 37 and the couch 31.

The patient support apparatus 60 also has a sensor unit 62 having sensor elements 63, 64 to detect a weight variable for determining the weight of a patient 14. The force transmission elements 61 are formed partially by one of the sensor elements 63 of the sensor unit 62 in each instance, the sensor elements 63, 64 being formed respectively by a piezo element. The piezo elements are used in each instance to detect a weight variable for determining the weight of a patient 14. The piezo elements can also be disposed on the base unit 35 of the travel unit 32. The piezo elements here at least partially form force transmission elements 65 of the travel unit 32, for example a force transmission element 65 (shown with a broken line in FIG. 3) formed by a suspension unit of the wheels.

Detection of the weight variable by the piezo elements takes place such that an electrical signal and/or and electrical voltage is applied for example within the piezo elements, so that the piezo elements are excited to oscillate at a frequency, the frequency being identical to a resonant frequency of the piezo elements. When loaded, in other words when there is a change in the force of the weight acting on the couch 31 and therefore on the piezo elements, for example due to the patient 14 being positioned on the couch 31, an oscillation characteristic of the incorporated piezo elements changes, resulting in a change in the resonant frequency and/or bandwidth, etc. This change is detected as a weight variable and represents a measure of the weight of the patient 14.

The sensor unit 62 also has further sensor elements 64 formed in each instance by piezo elements, which are formed by reference sensor elements and are designed to detect a reference weight variable. These further piezo elements are disposed on the lifting unit 33 or travel unit 32 in such a manner that they are positioned at the shortest distance from the two first sensor elements 63 but are disposed without load on the lifting unit 33 or travel unit 32. The arrangement of the reference sensor elements here can be the same as the arrangement of the reference sensor elements in FIG. 2.

A further mode of operation and a further structure of the sensor unit 61 and the patient support apparatus 60 are configured in the same way as in the description relating to FIG. 2.

It is also conceivable for the sensor unit 62 to have a first set of sensor elements 47, which are formed by strain gauges and are configured and disposed in the same way as in the description relating to FIG. 2, and a second set of sensor elements 63, which are formed by piezo elements and are configured and disposed in the same way as in the description relating to FIG. 3.

FIG. 4 shows a further alternative exemplary embodiment of the patient support apparatus 70. A couch 31 and travel unit 32 of the patient support apparatus 70 here are configured in the same way as in the exemplary embodiments relating to FIGS. 2 and 3. In the present exemplary embodiment a lifting unit 33 of the patient support apparatus 70 is also embodied in the same way as the lifting unit 33 in the exemplary embodiment relating to FIG. 2.

A sensor unit 71 of the patient support apparatus 70 has a first sensor element 72, which detects an energy variable of a drive unit 44 of the lifting unit 33. The sensor element 72 here is formed by an energy detection element and disposed on the drive unit 44. The weight of the patient 14 can be determined in the computation unit 49 based on the detection of an energy supply and/or a supply of electrical work to the lifting unit 33. A distance covered on the part of the couch 31 by the lifting unit 33 can also be detected, with the sensor unit 71 having a further sensor element 73 for this purpose.

The weight can also be determined based on a change in the supply of electrical work, to hold the couch 31 at a constant height when the total weight of the couch together with objects, for example a patient and/or local coils, positioned on the couch changes. Alternatively the energy variable can also be detected based on a lifting movement to be executed by the lifting unit 33, as required for the weight measurement.

Figure 5:
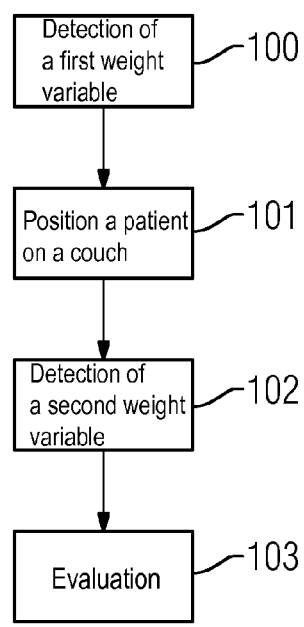

The sensor unit 71 also comprises a further sensor element 74, which is formed by a reference sensor element, for detecting a reference variable. The reference sensor element is disposed directly adjacent to the sensor element 72 for detecting the weight variable within the drive unit 44 but is only provided to detect the interference signals induced in the sensor element 72. An evaluation of the weight variables and reference variables detected by the sensor elements 72, 73, 74 and determination of the weight of the patient 14 take place in the same way as in the description in FIGS. 2 and 5.

The invention claimed is:

1. A patient support apparatus for a medical imaging apparatus, comprising:
    a couch for laying a patient;
    a lifting unit for vertically moving the couch;
    a travel unit;
    a sensor unit comprising a sensor element for detecting a weight variable for determining a weight of the patient; and
    a force transmission element that is disposed on one end of the lifting unit facing the couch,
    wherein the sensor element is disposed on the lifting unit and/or on the travel unit,
    and wherein the sensor unit further comprises a reference sensor element for detecting a reference variable generated within the sensor element to eliminate an interference signal from the weight variable, wherein the interference signal is generated due to magnetic field and/or gradient field applied in the medical imaging apparatus within the sensor element,
    and wherein the reference sensor element is configured to detect the interference signal before the sensor element detecting the weight variable of the patient when the medical imaging apparatus has been started up.

2. The patient support apparatus as claimed in claim 1, wherein the sensor element is formed at least partially by the force transmission element.

3. The patient support apparatus as claimed in claim 1, wherein the sensor element is disposed on a drive unit of the lifting unit.

4. The patient support apparatus as claimed in claim 1, wherein the sensor element is formed at least partially by a strain gauge.

5. The patient support apparatus as claimed in claim 1, wherein the sensor element is formed at least partially by a piezo element.

6. The patient support apparatus as claimed in claim 1, wherein the sensor element is formed at least partially by an energy detection element.

7. The patient support apparatus as claimed in claim 1, wherein the reference sensor element comprises a same structure of the sensor element.

8. The patient support apparatus as claimed in claim 7, wherein the sensor element and the reference sensor element are disposed directly adjacent to one another.

9. The patient support apparatus as claimed in claim 1, wherein the sensor unit comprises a signal filter unit that filters an interference signal of a sensor signal.

10. The patient support apparatus as claimed in claim 1, wherein the sensor unit comprises a computation unit.

11. The patient support apparatus as claimed in claim 1, wherein the sensor unit comprises a local coil detection unit.

12. The patient support apparatus as claimed in claim 1, further comprising an overload unit for determining a weight distribution on the couch based on at least two weight variables.

13. A medical imaging apparatus, comprising:
a patient support apparatus comprising:
a couch for laying a patient;
a lifting unit for vertically moving the couch;
a travel unit;
a sensor unit comprising a sensor element for detecting a weight variable for determining a weight of the patient; and
a force transmission element that is disposed on one end of the lifting unit facing the couch,
wherein the sensor element is disposed on the lifting unit and/or on the travel unit,
wherein the sensor unit further comprises a reference sensor element for detecting a reference variable generated within the sensor element to eliminate an interference signal from the weight variable,
wherein the interference signal is generated due to magnetic field and/or gradient field applied in the medical imaging apparatus within the sensor element, and
wherein the reference sensor element is configured to detect the interference signal before the sensor element detecting the weight variable of the patient when the medical imaging apparatus has been started up.

14. A method for determining a weight of a patient, comprising:
detecting a first weight variable by a sensor element of a sensor unit integrated within a lifting unit of a patient support apparatus;
laying the patient on a couch of the patient support apparatus;
detecting a second weight variable by the sensor element of the sensor unit, the second weight variable being different from the first weight variable due to a force of the weight of the patient acting on the couch; and
detecting a reference variable generated within the sensor element by a reference sensor element of the sensor unit,
wherein interference signals are eliminated from the first and/or the second weight variable based on the reference variable,
wherein the interference signal is generated due to magnetic field and/or gradient field applied in a medical imaging apparatus within the sensor element, and
wherein the interference signal is detected before detecting the weight variable of the patient when the medical imaging apparatus has been started up.

15. The method as claimed in claim 14, wherein the first weight variable and the second weight variable are detected at two different positions on the patient support apparatus for determining a weight distribution on the couch, and wherein a warning signal is generated and output if the weight distribution is irregular.

* * * * *